United States Patent [19]

Guglielmetti

[11] 4,245,007

[45] Jan. 13, 1981

[54] 1,4-BIS-[AZOL-2'-YL]-NAPHTHALENES AND PROCESS OF USING THE SAME

[75] Inventor: Leonardo Guglielmetti, Basel, Switzerland

[73] Assignee: Ciba-Geigy Corporation, Ardsley, N.Y.

[21] Appl. No.: 930,111

[22] Filed: Aug. 1, 1978

Related U.S. Application Data

[63] Continuation of Ser. No. 727,119, Sep. 27, 1976, abandoned.

[30] Foreign Application Priority Data

Oct. 10, 1975 [CH] Switzerland ................ 13213/75

[51] Int. Cl.³ .................. B32B 27/36; D06L 3/12; C11D 9/44
[52] U.S. Cl. .................. 428/480; 252/301.28; 252/543; 427/158; 428/90; 428/265; 428/290; 548/224
[58] Field of Search ............. 252/89 R, 89 OB, 543, 252/301.28, 301.27; 264/204; 260/307 D; 427/158; 548/224

[56] References Cited

U.S. PATENT DOCUMENTS

| | | | |
|---|---|---|---|
| 3,336,330 | 8/1967 | Schinzel et al. | 260/307 D |
| 3,575,996 | 4/1971 | Liechti et al. | 260/307 D |
| 3,641,051 | 2/1972 | Frischkorn et al. | 260/309.2 |
| 3,709,896 | 1/1973 | Frischkorn et al. | 260/370 D |
| 3,993,659 | 11/1976 | Meyer | 260/307 D |
| 4,048,185 | 9/1977 | Pintschovious et al. | 260/307 D |

FOREIGN PATENT DOCUMENTS

| | | | |
|---|---|---|---|
| 1302052 | 11/1969 | Fed. Rep. of Germany | 260/307 D |
| 670890 | 5/1971 | Fed. Rep. of Germany . | |
| 1955310 | 5/1971 | Fed. Rep. of Germany | 252/301.2 W |
| 1563184 | 3/1969 | France | 260/307 D |
| 2036652 | 12/1970 | France | 260/307 D |
| 1163851 | 9/1969 | United Kingdom | 260/307 D |

*Primary Examiner*—P. E. Willis, Jr.
*Attorney, Agent, or Firm*—Prabodh I. Almaula; Edward McC. Roberts

[57] ABSTRACT

New 1,4-bis-[azol-2'-yl]-naphthalene compounds, a process for their preparation as well as a process for optically brightening organic materials on using said compounds are disclosed.

10 Claims, No Drawings

1,4-BIS-[AZOL-2'-YL]-NAPHTHALENES AND PROCESS OF USING THE SAME

This is a continuation of application Ser. No. 727,119 filed on Sept. 27, 1976 now abandoned.

The present invention relates to new 1,4-bis-[azol-2'-yl]-naphthalenes, a process for their manufacture and their use for optically brightening organic materials, and to washing agents containing these compounds.

The new 1,4-bis-[azol-2'-yl]-naphthalenes correspond to the formula

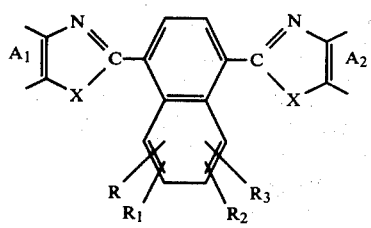

wherein $A_1$ and $A_2$ independently of one another denote ring systems of benzene, naphthalene or tetrahydronaphthalene which are unsubstituted or contain non-chromophoric substituents and are fused to the azole ring, R denotes halogen, alkyl with 1 to 12 carbon atoms, alkoxy with 1 to 18 carbon atoms, alkenyl with 3 or 4 carbon atoms, cyano, cycloalkyl, phenylalkyl with 1 to 4 carbon atoms in the alkyl part, aralkoxy with 1 to 4 carbon atoms in the alkoxy part, phenyl, phenoxy, arylsulphonyl, alkylsulphonyl with 1 to 8 carbon atoms, $-SO_2NY_1Y_2$, wherein $Y_1$ and $Y_2$ independently of one another represent hydrogen or optionally substituted alkyl with 1 to 8 carbon atoms, or $Y_1$ and $Y_2$, together with the nitrogen atom to which they are linked, form a heterocyclic ring, which can optionally contain yet further hetero-atoms in the ring and can optionally also be substituted, $SO_3M$, wherein M represents hydrogen or a salt-forming cation, or $-COOY$, wherein Y represents hydrogen, a salt-forming cation or alkyl with 1 to 8 carbon atoms, or R, conjointly with $R_1$, denotes the remaining part of a fused benzene ring, $R_1$ denotes hydrogen, halogen, alkyl with 1 to 12 carbon atoms, alkoxy with 1 to 18 carbon atoms, alkenyl with 3 or 4 carbon atoms or aralkoxy with 1 to 4 carbon atoms in the alkoxy part, or $R_1$ conjointly with R denotes the remaining part of a fused benzene ring, $R_2$ denotes hydrogen, halogen or alkyl with 1 to 12 carbon atoms, $R_3$ denotes hydrogen or halogen and X denotes oxygen or $=N-Z$, wherein Z denotes hydrogen or unsubstituted or hydroxysubstituted or cyano-substituted alkyl with 1 to 4 carbon atoms, alkenyl with 3 or 4 carbon atoms, aralkyl with 1 to 4 carbon atoms in the alkyl part or alkanoyl with 2 to 5 carbon atoms.

Examples of non-chromophoric substituents are alkyl with 1 to 18, and preferably 1 to 4, carbon atoms, hydroxyl, cyano, chlorine, sulpho, carboxyl, alkoxy with 1 to 18, and preferably 1 to 4, carbon atoms, aryloxy, aralkoxy, alkenyloxy, carbalkoxy with 2 to 9, and preferably 2 to 5, carbon atoms, cycloalkyl with 5 to 7 ring members, preferably cyclohexyl, aralkyl with 1 to 4 carbon atoms in the alkyl part and alkylsulphonyl with 1 to 8 carbon atoms.

Possible substituents of the alkyl groups $Y_1$ and $Y_2$ are, inter alia, hydroxyl, cyano, halogen and alkoxy.

"Carboxyl" and "sulpho" are to be understood as the radicals $-COOM$ and $-SO_3M$ respectively, wherein M represents hydrogen or a salt-forming cation. Possible salt-forming cations M are, in general, those of the alkaline earth metals, for example calcium, barium or magnesium, as well as, in particular, of alkali metals, such as, for example, sodium or potassium, but also unsubstituted ammonium or ammonium substituted by alkyl or hydroxyalkyl with 1 to 4 carbon atoms, or amine salt ions of cyclic amines, such as pyridine, morpholine and piperidine. Preferred meanings of M are, in addition to hydrogen, especially the sodium and potassium cations.

1,4-Bis-[oxazol-2'-yl]-naphthalenes of the formula

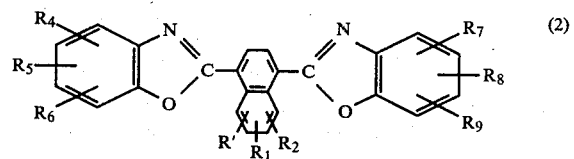

wherein R' denotes halogen, alkyl with 1 to 12 carbon atoms, alkoxy with 1 to 18 carbon atoms, cycloalkyl, phenylalkyl with 1 to 4 carbon atoms in the alkyl part, alkenyl with 3 or 4 carbon atoms, aralkoxy with 1 to 4 carbon atoms in the alkyl part, phenyl, phenoxy, alkylsulphonyl with 1 to 8 carbon atoms in the alkyl part, $-SO_2NY_1Y_2$, wherein $Y_1$ and $Y_2$ independently of one another represent hydrogen or optionally substituted alkyl with 1 to 8 carbon atoms, or $Y_1$ and $Y_2$, together with the nitrogen atom to which they are linked, form a heterocyclic ring which optionally can contain yet further heteroatoms in the ring and optionally can also be substituted, $SO_3M$, wherein M represents hydrogen or a salt-forming cation, or $-COOY$, wherein Y represents hydrogen, a salt-forming cation or alkyl with 1 to 8 carbon atoms, or R' conjointly with $R_1$ denotes the remaining part of a fused benzene ring, $R_1$ denotes hydrogen, halogen, alkyl with 1 to 12 carbon atoms, alkoxy with 1 to 18 carbon atoms, alkenyl with 3 or 4 carbon atoms or aralkoxy with 1 to 4 carbon atoms in the alkoxy part, or $R_1$ conjointly with R' denotes the remaining part of a fused benzene ring, $R_2$ denotes hydrogen, halogen or alkyl with 1 to 12 carbon atoms, $R_4$ and $R_7$ independently of one another denote hydrogen, halogen, alkyl with 1 to 18 carbon atoms which is unsubstituted or substituted by halogen, hydroxyl, alkoxy with 1 to 4 carbon atoms, $-COOY$, wherein Y represents hydrogen, a salt-forming cation or alkyl with 1 to 8 carbon atoms, or $-CONY_1Y_2$, wherein $Y_1$ and $Y_2$ independently of one another represent hydrogen or alkyl with 1 to 8 carbon atoms, or denote alkoxy with 1 to 18 carbon atoms, cycloalkyl, phenyl, phenoxy or phenylalkyl which has 1 to 4 carbon atoms in the alkyl part and is unsubstituted or substituted by alkyl with 1 to 4 carbon atoms, or alkenyl with 3 or 4 carbon atoms, aralkoxy with 1 to 4 carbon atoms in the alkoxy part, cyano, carbalkoxy with 1 to 8 carbon atoms in the alkyl part, cyanoalkyl with a total of 2 to 5, and preferably 4, carbon atoms, $-COOY$, wherein Y represents hydrogen or a salt-forming cation, $-CONY_1Y_2$, wherein $Y_1$ and $Y_2$ independently of one another denote hydrogen or alkyl with 1 to 8 carbon atoms, $-SO_3M$, wherein M represents hydrogen or a salt-forming cation, or $-SO_2NY_1Y_2$, wherein $Y_1$ and $Y_2$ have the abovementioned meaning, or alkylsulphonyl with 1 to 8 carbon atoms or arylsulphonyl, $R_5$ and $R_8$ independently of one another denote hydrogen, halogen or alkyl with 1 to 18 carbon atoms which is unsubstituted or substituted by halogen, hydroxyl, alkoxy with 1 to 4 carbon atoms, —COOY, wherein Y represents hydrogen, a salt-forming cation or alkyl with 1 to 8 carbon atoms, or —$CONY_1Y_2$, wherein $Y_1$ and $Y_2$ independently of one another represent hydrogen or alkyl with 1 to 8 carbon atoms, or denote alkoxy with 1 to 18 carbon atoms, phenylalkyl which has 1 to 4 carbon atoms in the alkyl part and is unsubstituted or substituted by alkyl with 1 to 4 carbon atoms, or alkenyl with 3 or 4 carbon atoms, aralkoxy with 1 to 4 carbon atoms in the alkoxy part, cyano, carbalkoxy with 1 to 8 carbon atoms in the alkyl part or cyanoalkyl with a total of 2 to 5, and preferably 4, carbon atoms, and $R_4$ and $R_5$, and $R_7$ and $R_8$, in the ortho-position relative to one another also denote the tetramethylene or 1,3-butadienylene radical and $R_6$ and $R_9$ independently of one another denote hydrogen, halogen or alkyl with 1 to 4 carbon atoms, are within the scope of the formula (I).

1,4-Bis-[oxazolyl-2′-yl]-naphthalenes of the formula

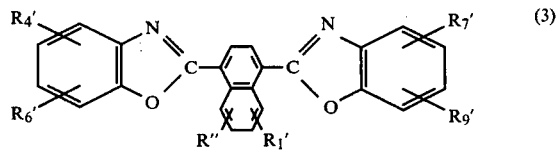

(3)

wherein R″ denotes halogen, alkyl with 1 to 12 carbon atoms, alkoxy with 1 to 12 carbon atoms, alkylsulphonyl with 1 to 4 carbon atoms, —$SO_2M$, wherein M represents hydrogen or a salt-forming cation, or —$SO_2NY_1Y_2$, wherein $Y_1$ and $Y_2$ independently of one another represent hydrogen or optionally substituted alkyl with 1 to 8 carbon atoms, or $Y_1$ and $Y_2$ together with the nitrogen atom to which they are linked form a 5-membered or 6-membered heterocyclic ring which optionally can also contain an oxygen atom or a further nitrogen atom as a ring member and optionally can be substituted by alkyl or hydroxyalkyl, each with 1 to 8 carbon atoms, $R_1′$ denotes hydrogen, halogen, alkyl with 1 to 12 carbon atoms or alkoxy with 1 to 12 carbon atoms, $R_4′$ and $R_7′$ independently of one another denote hydrogen, halogen, alkyl with 1 to 12 carbon atoms, alkoxy with 1 to 12 carbon atoms, —COOY, wherein Y represents hydrogen, a salt-forming cation or alkyl with 1 to 8 carbon atoms, —$CONY_1Y_2$, wherein $Y_1$ and $Y_2$ independently of one another represent hydrogen or alkyl with 1 to 8 carbon atoms, or alkylsulphonyl with 1 to 8 carbon atoms, carboxyalkyl with 1 to 4 carbon atoms in the alkyl part, or its alkyl ester with 1 to 4 carbon atoms, —$SO_3M$, wherein M represents hydrogen or a salt-forming cation, or —$SO_2NY_1Y_2$, wherein $Y_1$ and $Y_2$ have the abovementioned meaning, or phenylalkyl with 1 to 4 carbon atoms in the alkyl part, and $R_6′$ and $R_9′$ denote hydrogen, chlorine or alkyl with 1 to 4 carbon atoms, are of particular importance.

1,4-Bis-[oxazol-2′-yl]-naphthalenes which are of particular interest in practice are those of the formula

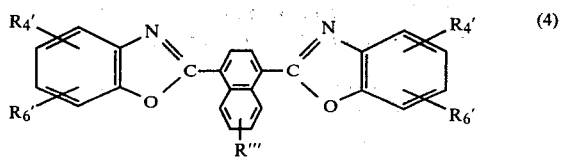

(4)

wherein R‴ denotes chlorine, bromine, alkyl with 1 to 4 carbon atoms, alkoxy with 1 to 4 carbon atoms or alkylsulphonyl with 1 to 4 carbon atoms, or denotes —$SO_3M$, wherein M represents hydrogen or an alkali metal, alkaline earth metal, ammonium or amine salt ion, or —$SO_2NY_1Y_2$, wherein $Y_1$ and $Y_2$ independently of one another represent hydrogen or alkyl with 1 to 4 carbon atoms which is optionally substituted by hydroxyl or halogen, or $Y_1$ and $Y_2$ together with the nitrogen atom to which they are linked form a morpholine ring or a piperazine ring which is optionally substituted by alkyl and/or hydroxyalkyl, $R_4′$ denotes hydrogen, halogen, alkyl with 1 to 12 carbon atoms, alkoxy with 1 to 12 carbon atoms, —COOY, wherein Y represents hydrogen, a salt-forming cation or alkyl with 1 to 8 carbon atoms, —$SO_3M$, wherein M represents hydrogen or a salt-forming cation, or —$CONY_1Y_2$, wherein $Y_1$ and $Y_2$ independently of one another represent hydrogen or alkyl with 1 to 8 carbon atoms, or denotes alkylsulphonyl with 1 to 8 carbon atoms, carboxylalkyl with 1 to 4 carbon atoms in the alkyl part, or its alkyl ester with 1 to 4 carbon atoms, or —$SO_2NY_1Y_2$, wherein $Y_1$ and $Y_2$ have the abovementioned meaning, or denotes phenylalkyl with 1 to 4 carbon atoms in the alkyl part and $R_6′$ denotes hydrogen, chlorine or alkyl with 1 to 4 carbon atoms, those of the formula

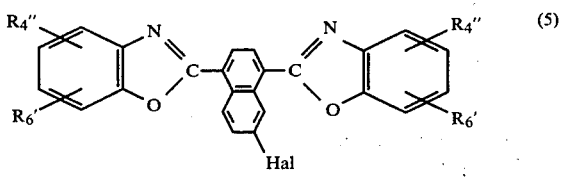

(5)

wherein Hal denotes chlorine or bromine, $R_4″$ denotes hydrogen, halogen, alkyl with 1 to 8 carbon atoms, alkoxy with 1 to 8 carbon atoms, —COOY, wherein Y represents hydrogen, a salt-forming cation or alkyl with 1 to 4 carbon atoms, —$SO_3M$, wherein M represents hydrogen or a salt-forming cation, alkylsulphonyl with 1 to 4 carbon atoms, carboxyalkyl with 1 to 4 carbon atoms in the alkyl part, or its alkyl ester with 1 to 4 carbon atoms, phenylalkyl with 1 to 4 carbon atoms in the alkyl part or —$SO_2NY_1Y_2$ or —$CONY_1Y_2$, wherein $Y_1$ and $Y_2$ independently of one another represent hydrogen or alkyl with 1 to 4 carbon atoms and $R_6′$ denotes hydrogen, chlorine or alkyl with 1 to 4 carbon atoms, those of the formula

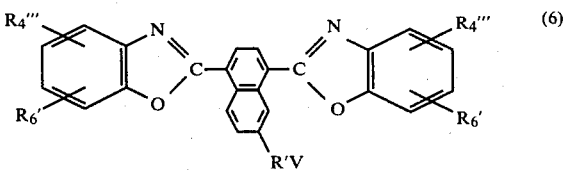

(6)

wherein $R^{IV}$ denotes chlorine, alkyl with 1 to 4 carbon atoms, alkylsulphonyl with 1 to 4 carbon atoms or —SO$_3$M, wherein M represents hydrogen or an alkali metal, alkaline earth metal, ammonium or amine salt ion, or denotes —SO$_2$NY$_1$Y$_2$, wherein Y$_1$ and Y$_2$ independently of one another represent hydrogen or alkyl or hydroxyalkyl, each with 1 to 4 carbon atoms, R$_4'''$ denotes hydrogen, halogen in the 5-position or 6-position, alkyl with 1 to 4 carbon atoms or —COOY, wherein Y represents hydrogen, a salt-forming cation or alkyl with 1 to 4 carbon atoms, or denotes alkylsulphonyl with 1 to 4 carbon atoms and R$_6'$ denotes hydrogen, chlorine or alkyl with 1 to 4 carbon atoms, and also those of the formula

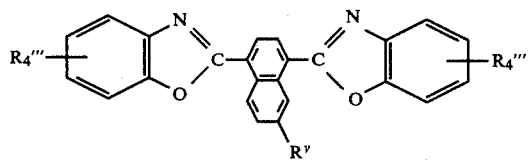

(7)

wherein R$^\nu$ denotes chlorine, bromine, alkyl with 1 to 4 carbon atoms or —SO$_3$M, wherein M represents hydrogen or an alkali metal, alkaline earth metal, ammonium or amine salt ion, or denotes alkylsulphonyl with 1 to 4 carbon atoms and R$_4'''$ denotes hydrogen, halogen in the 5-position or 6-position, alkyl with 1 to 4 carbon atoms or —COOY, wherein Y represents hydrogen, a salt-forming cation or alkyl with 1 to 4 carbon atoms, or denotes alkylsulphonyl with 1 to 4 carbon atoms.

Compounds which are distinguished by particularly outstanding properties are those of the formula

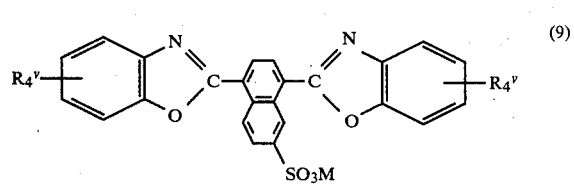

(8)

wherein R$_4''''$ denotes hydrogen or, in the 5-position or 6-position, alkyl with 1 to 4 carbon atoms or —COOY, wherein Y represents alkyl with 1 to 4 carbon atoms, and of the formula

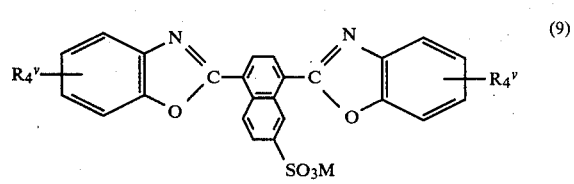

(9)

wherein R$_4^\nu$ denotes hydrogen or, in the 5-position or 6-position, alkyl with 1 to 4 carbon atoms or —COOY, wherein Y represents hydrogen, an alkali metal, alkaline earth metal, ammonium or amine salt ion or alkyl with 1 to 4 carbon atoms, and M denotes an alkali metal, alkaline earth metal, ammonium or amine salt ion, and amongst these the compounds of the formulae

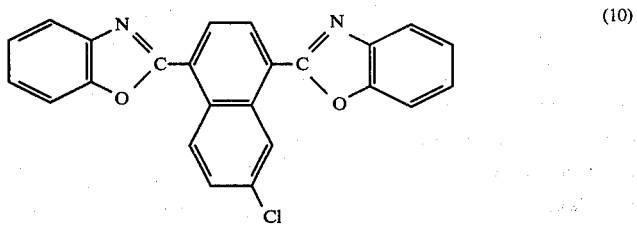

(10)

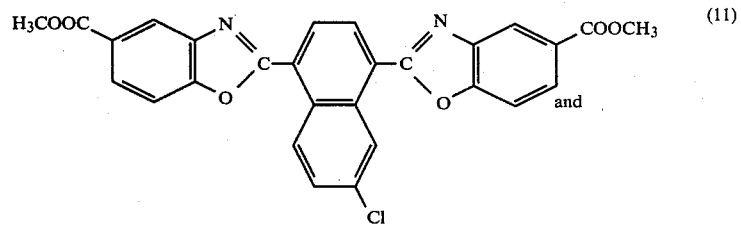

(11)

and

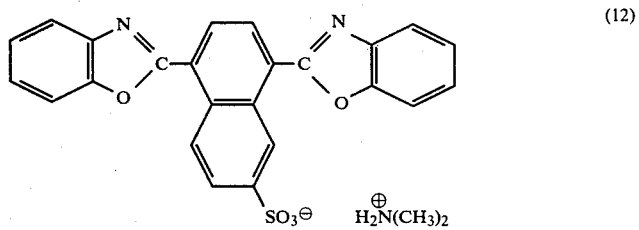

(12)

may also be singled out.

The 1,4-bis-[azol-2'-yl]-naphthalenes of the formula (1) can be manufactured by various processes which are in themselves known. A preferred process is characterised in that one mol equivalent of a compound of the formula

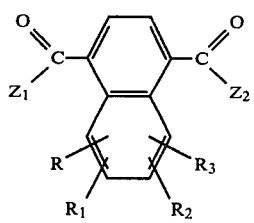

wherein R, $R_1$, $R_2$ and $R_3$ have the abovementioned meaning and $Z_1$ and $Z_2$ independently of one another denote hydroxyl, halogen or alkoxy with 1 to 4 carbon atoms, is reacted with 2 mol equivalents of an amino compound of the formula

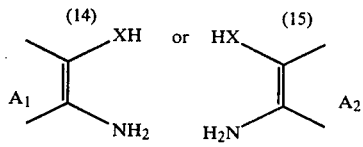

wherein $A_1$, $A_2$ and X have the abovementioned meaning, or with one mol equivalent of each of these amino compounds, at temperatures between 120° and 350° C.

Depending on whether it is intended to manufacture an asymmetrical or symmetrical type of compound, $Z_1 \neq Z_2$ or $Z_1 = Z_2$ will be chosen and it is appropriate to give preference to functional groups of markedly different reactivity, for example the acid ester chloride, in the case where $Z_1 \neq Z_2$ and to compounds which are as reactive as possible, that is to say, for example, the dicarboxylic acid chloride, in the case where $Z_1 = Z_2$.

For the manufacture of symmetrical compounds, a compound of the formula (13) wherein $Z_1$ and $Z_2$ are identical, is reacted with 2 mol equivalents of a compound of the formula (14) or (15) and the resulting acyl compound of the formula

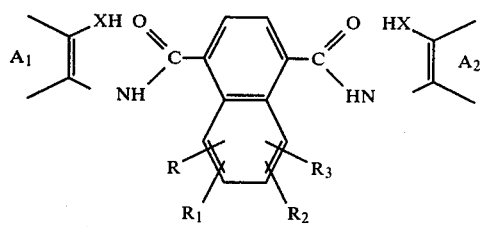

wherein $A_1$ and $A_2$ are identical, is subjected to cyclisation by heating to temperatures above 100° C. in the presence or absence of a catalyst.

If it is desired to prepare compounds of an asymmetric type, it is then appropriate first to effect, analogously to the method described above, cyclisation on one side of the primary condensation product of the formula

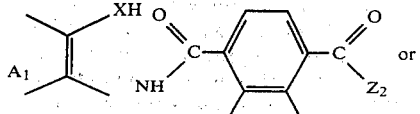

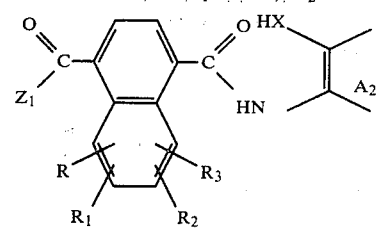

wherein $A_1$, $A_2$, R, $R_1$, $R_2$, $R_3$, $Z_1$, $Z_2$ and X have the abovementioned meaning and $A_1$ differs from $A_2$, to give compounds of the formulae respectively and then to repeat the analogous reaction sequence on the remaining carboxyl functional group $$-C\overset{O}{\underset{Z_1}{\diagdown}} \quad \text{or} \quad -C\overset{O}{\underset{Z_2}{\diagdown}}$$

using one of the various amine compounds of the formula (15) or (14) used in the first stage.

In principle, the manufacture of compounds of the formula (1) to (12) can also be carried out by a single stage process starting from o-aminophenols or from o-phenylenediamines of the formulae (14) and (15) and naphthalene-1,4-dicarboxylic acid derivatives of the formula (13) by heating these components together to relatively high temperatures, appropriately of between 120° and 350° C., in an inert gas (for example a stream of nitrogen). This reaction is preferably carried out in the presence of dehydrating agents, in the same way as described above for the end stage.

In order to manufacture compounds of a symmetrical type, the reaction is preferably carried out in two stages by first subjecting o-aminophenols or o-phenylenediamines of the formulae (14) and (15) and naphthalenedicarboxylic acid compounds of the formula (13) (wherein $Z_1=Z_2$) to a condensation reaction to give acyl compounds of the formula (16). The naphthalenedicarboxylic acid chlorides are appropriately used for this reaction and are subjected, at temperatures between 100° and 220° C., to a condensation reaction with the o-aminophenols or o-phenylenediamines in the presence of an organic solvent, such as toluene, xylene, chlorobenzene, dichlorobenzene, trichlorobenzene, nitrobenzene or in an inert amine, such as pyridine, picolines, triethylamine, quinoline, N,N-dimethylaniline and the like, which bind the hydrogen halide which is liberated, and the resulting acyl compounds of the formula (16) are then converted, at temperatures between 120° and 350° C., in the presence or absence of a catalyst, into the azole derivatives. If carboxylic acid chlorides are used as starting materials, these can be manufactured, immediately prior to the condensation reaction with the o-aminophenol or o-phenylenediamine and without precipitation, from the free carboxylic acid and thionyl chloride, optionally with the addition of a catalyst, such as pyridine, in the solvent in which the condensation reaction subsequently takes place.

Suitable dehydrating agents—including catalysts which have a dehydrating action—are, for example, boric acid, boric anhydride, zinc chloride, p-toluenesulphonic acid, phosphorus oxychloride, thionyl chloride and also polyphosphoric acids, including pyrophosphoric acid. High-boiling, polar organic solvents, such as, for example, dimethylformamide, dichlorobenzene, trichlorobenzene, chlorinated biphenyl and aliphatic, optionally etherified hydroxy compounds, for example propylene glycol and ethylene glycol monoethyl ether, and high-boiling esters of phthalic acid, such as, for example dibutyl phthalate, can also be used in addition.

A particularly advantageous process for the manufacture of symmetrical compounds of the formulae (2) to (12) consists, for example, in subjecting the acyl compounds, which have been obtained by the condensation reaction of 2 mols of o-aminophenols of the formulae

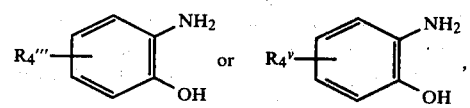

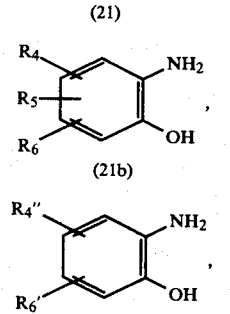

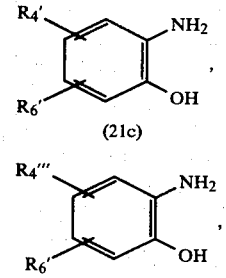

wherein $R_4$ to $R_6$, $R_4'$, $R_4''$, $R_4'''$, $R_4^v$ and $R_6'$ have the indicated meaning, with the corresponding naphthalene-1,4-dicarboxylic acid chloride in the presence of dehydrating agents, without isolation, to an azole cyclisation reaction by treatment with the same dehydrating agent as that used in the preliminary stage, at temperatures between 120° and 350° C.

Amongst further possible manufacturing processes there may be mentioned the reaction of correspondingly substituted 1,4-dicyanonaphthalenes with o-aminophenols or o-phenylenediamines of the formulae (14) and (15) at elevated temperatures, preferably of 160° to 260° C. This reaction is appropriately carried out in the presence of agents which bind ammonia, such as, for example, phosphoric acid, polyphosphoric acid or phosphorus pentoxide, under an inert gas.

Another manufacturing process, which is advantageous in many cases, for compounds of the formulae (2) to (12), for example the compound of the formula (2), is a condensation reaction of o-halogenoanilines with a compound of the formula (13) in accordance with the equation

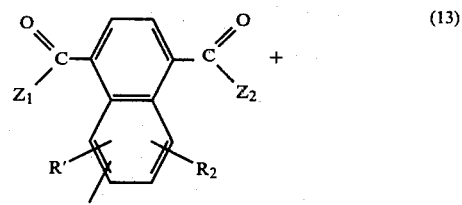

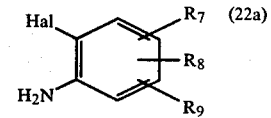

by methods which are in themselves known to give the corresponding acid amide of the formula

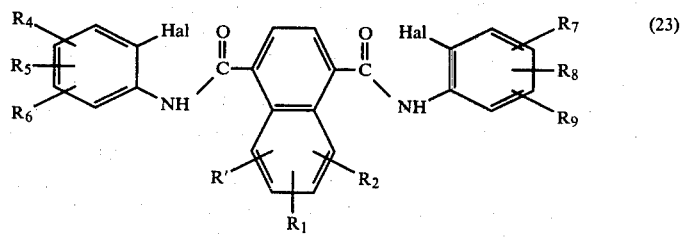

and subsequent cyclisation to give the corresponding bis-benzoxazolyl derivative. In this case, the cyclisation reaction is carried out in the presence of polar solvents which are chemically inert towards the reactants, and also in the presence of agents which bind a hydrogen halide and of copper catalysts. In the above formulae, Hal denotes chlorine or bromine, whilst all the other symbols have the meaning indicated further above.

This manufacturing process proves to be particularly appropriate for the preparation of symmetrical compounds of the formulae (2) to (12).

Examples which may be mentioned of polar solvents which are chemically inert towards the reactants are dimethylformamide, dimethylsulphoxide, N-methylpyrrolidone or nitrobenzene. Hydrogen halide-binding agents which may be mentioned are: an alkali metal acetate, magnesium oxide and organic bases, such as pyridine and the like. Examples of copper catalysts which may be mentioned are copper-I chloride, copper-II chloride, copper acetate, copper oxides and elementary finely divided copper and the like.

Resulting compounds of the formulae (2) to (12) can also subsequently be converted into one another by known methods, such as, for example, by forming a salt or by esterification, amidation, saponification and the like.

The starting materials of the formulae (14) and (15) are known or are manufactured analogously to processes which are in themselves known.

Some of the starting materials of the formula (13) are known and are also manufactured analogously to processes which are in themselves known. However, it is also possible to manufacture these compounds and the new compounds of the formula (13) by subjecting correspondingly substituted o-xylylene dicyanides to a condensation reaction with glyoxal in an alkaline medium and saponifying the resulting 1,4-dicyanonaphthalenes under acid or alkaline conditions to give the correspondingly substituted naphthalene-1,4-dicarboxylic acids and optionally converting the latter in a manner which is in itself known into the corresponding acid halides (compare German Offenlegungsschrift No. 2,550,521).

The arylsulphonyl-aminophenols are obtained, for example, in accordance with examples in British Patent No. 743,907, whilst the manufacture of some 4-alkylsulphonyl-2-aminophenols has been described by D. Simov [C.A. 66 (1967) 115,401m]. The 5-alkylsulphonyl-2-aminophenols can be manufactured analogously to 5-methylsulphonyl-2-aminophenol. With this manufacturing route, the 1,3-benzoxazolones which can be employed in place of these aminophenols are obtained as an intermediate.

In the dissolved or finely divided state, the new compounds defined above display a more or less pronounced fluorescence. They are used for optically brightening very diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high-molecular materials:

(a) Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on α,β-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example ethylene, propylene, styrenes or dienes and also so-called ABS polymers), and polymers based on vinyl and vinylidene compounds (such as, for example, vinyl chloride, vinyl alcohol and vinylidene chloride), (b) Polymerisation products which are obtainable by ring opening, for example, polyamides of the polycaprolactam type, and also polymers which are obtainable both via polyaddition and via polycondensation, such as polyethers or polyacetals, (c) Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyester) or unsaturated (for example maleic acid-dialcohol polycondensates as well as their crosslinking products with copolymerisable vinyl monomers), unbranched and branched (also including those based on polyhydric alcohols, such as, for example alkyd resins) polyesters, polyamides (for example hexamethylenediamine adipate), maleate resins, melamine resins, their precondensates and analogues, polycarbonates and silicones, and (d) Polyaddition products such as polyurethanes (crosslinked and non-crosslinked) and epoxide resins.

II. Semi-synthetic organic materials, for example, cellulose esters of varying degrees of esterification (so-called 2½ acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, natural lacquer resins, starch and casein.

Preferred organic materials are those made of polyester, polyethylene, polypropylene, polystyrene, polyacrylonitrile, polyurethane, polyvinyl chloride and acetylcellulose.

The organic materials to be optically brightened can be in the most diverse states of processing (raw materials, semi-finished goods or finished goods). On the other hand, they can be in the form of structures of the most diverse shapes, that is to say, for example, in the form of predominantly three-dimensional bodies such as sheets, profiles, injection mouldings, various machined articles, chips, granules or foams, and also as predominantly two-dimentional bodies such as films, foils, lacquers, coatings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper compositions.

The compounds to be used according to the invention are of importance, inter alia, for the treatment of organic textile materials, especially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finley divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C., for example at the boiling point of the bath or near it (about 90° C.). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

(a) Mixed with dyestuffs (shading) or pigments (coloured pigments or especially, for example, white pigments), or as an additive to dyebaths, printing pastes, discharge pastes or reserve pastes, and also for the after-treatment of dyeings, prints or discharge prints, (b) Mixed with so-called "carriers", wetting agents, plasticisers, swelling agents, antioxidants, light protection agents, heat stabilisers and chemical bleaching agents (chlorite bleach or bleaching bath additives), (c) Mixed with crosslinking agents or finishing agents (for example starch or synthetic finishes), and in combination with the most diverse textile finishing processes, especially synthetic resin finishes (for example crease-proof finishes such as "wash-and-wear", "permanent-press" or "no-iron"), as well as flameproof finishes, soft handle finishes, anti-soiling finishes or anti-static finishes, or antimicrobial finishes, (d) Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather, (e) As additives to so-called "master batches", (f) As additives to the most diverse industrial products in order to render these more marketable (for example improving the appearance of soaps, detergents and pigments), (g) In combination with other optically brightening substances, (h) In spinning bath preparations, that is to say as additives to spinning baths such as are used for improving the slip for the further processing of synthetic fibres, or from a special bath before the stretching of the fibre, (i) As scintillators for various purposes of a photographic nature, such as, for example, for electrophotographic reproduction or supersensitisation, and for the optical brightening of photographic layers, optionally in combination with white pigments such as, for example, $TiO_2$, and (k) Depending on the substituents, as laser dyestuffs.

If the brightening process is combined with textile treatment methods or finishing methods, the combined treatment can in many cases advantageously be carried out with the aid of appropriate stable preparations, which contain the optically brightening compounds in such a concentration that the desired brightening effect is achieved.

In certain cases, the brighteners are made fully effective by an after-treatment. This can, for example, be a chemical treatment (for example acid treatment), a thermal treatment (for example heat) or a combined chemical/thermal treatment. Thus, for example, the appropriate procedure to follow in optically brightening a series of fibre substrates, for example of polyester fibres, with the brighteners according to the invention is to impregnate these fibres with the aqueous dispersions (or optionally also solutions) of the brighteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. and up to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are preferably of interest.

The brighteners according to the invention can also be employed as a mixture with other brighteners. Since some of the brighteners according to the invention produce brightening effects with a green shade it is particularly advantageous to use them together with brighteners which show reddish-tinged brightening effects. Examples of the latter are compounds of the category of α,β-[benzoxazol-2-yl]-ethylenes and of the 2-stilbenyl-naphthotriazoles.

The new optical brightening agents are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying, to the washing powder or during the preparation of liquid washing agent combinations. They can be added either in the form of a solution or dispersion in water or other solvents or, without auxiliaries, as a dry brightening powder. For example, the brightening agents can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances, such as, for example, soap in the form of chips and powders, synthetics, soluble salts of sulphonic acid half-esters of higher fatty alcohols, arylsulphonic acids with higher and/or multiple alkyl substituents, sulphocarboxylic acid esters of medium to high alcohols, fatty acid acylaminoalkyl- or acylaminoaryl-glycerinesulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminetetraacetic acid, and foam stabilisers such as alkanolamides of higher fatty acids. The washing agents can further contain for example: antistatic agents, superfatting skin protection agents, such as lanolin, enzymes, antimicrobial agents, perfumes and dyestuffs.

The new optical brighteners have the particular advantage that they are also active in the presence of active chlorine donors, such as, for example, hypochlorite, and can be used without significant loss of the effects in wash liquors containing non-ionic washing agents, for example alkylphenol polyglycol ethers.

The compounds according to the invention are added in amounts of 0.005–1% or more, relative to the weight of the liquid or pulverulent finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out as follows, for example:

The textiles indicated are treated for 1 to 30 minutes at 20° to 100° C. in a wash liquor which contains 1 to 10 g/kg of a built-up composite washing agent and 0.05 to 1%, relative to the weight of the washing agent, of the claimed brightening agents. The liquor ratio can be 1:3 to 1:50. After washing, the textiles are rinsed, and dried, in the usual manner. The wash liquor can contain 0.2 g/l of active chlorine (for example as hypochlorite) or 0.1 to 2 g/l of sodium perborate as a bleaching additive.

In the examples the parts, unless otherwise stated, are always parts by weight and the percentages are always percentages by weight. Unless otherwise noted, melting points and boiling points are uncorrected.

EXAMPLE 1

12.5 g of 6-chloro-naphthalene-1,4-dicarboxylic acid in 200 ml of toluene are heated with 18 g of thionyl chloride and 0.5 g of dimethylformamide for two hours under reflux. Whilst nitrogen is passed into the mixture, 75 ml of toluene are distilled off and replaced with fresh toluene. A solution of 10.9 g of 2-aminophenol and 18.2 g of dimethylaniline in 100 ml of toluene is added in the course of 15 minutes, at 70° to 80° C., to the acid chloride solution which has been obtained and the reaction mixture is stirred at this temperature for two hours. Half of the toluene is then distilled off, whilst passing nitrogen into the mixture, and 300 ml of 1,2,4-trichlorobenzene and 2 g of zinc chloride are added to the residue. The toluene which is still present is distilled off whilst passing in nitrogen and the reaction mixture is heated to 210° C. for two hours, during which time 200 ml of trichlorobenzene and water distil off. The mixture which remains is concentrated to dryness in vacuo and the residue is recrystallised from tetrachloroethylene with the aid of active charcoal. 10 g, corresponding to 56% of theory, of the compound of the formula

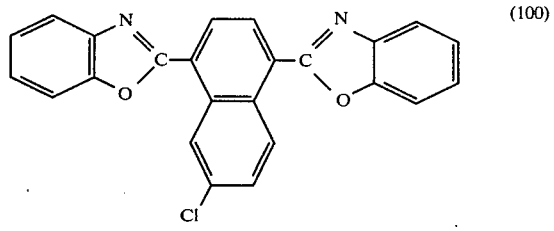

(100)

are obtained in the form of pale yellow needles with a melting point of 205° to 208° C. After recrystallising once from tetrachloroethylene, the product melts at 210° to 212° C.

Analysis: $C_{24}H_{13}N_2O_2Cl$. Calculated: C, 72.64; H, 3.30; N, 7.06; Cl, 8.93. Found: C, 72.37; H, 3.41; N, 7.08; Cl, 9.32.

The compounds of the formula

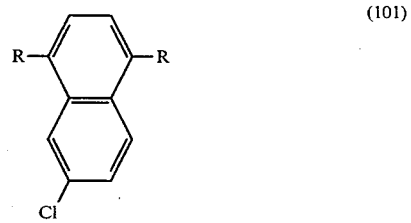

(101)

which are listed in Table I are manufactured in an analogous manner from 6-chloro-naphthalene-1,4-dicarboxylic acid and correspondingly substituted 2-aminophenols.

TABLE I

| Compound No. | Structure of R | Melting point, °C. |
|---|---|---|
| (102) | H₃COOC-[benzoxazole] | 253–255 |
| (103) | H₅C₂OOC-[benzoxazole] | 234–235 |
| (104) | H₃COOC-[benzoxazole] | 293–294 |
| (105) | Cl-[benzoxazole] | 262–263 |
| (106) | H₅C₂—O₂S-[benzoxazole] | 260–261 |
| (107) | (H₃C)₃C-[benzoxazole] | 198–199 |
| (108) | H₃C-[benzoxazole]-CH₃ | 223–224 |

EXAMPLE 2

13.6 g of 6-tert.-butyl-naphthalene-1,4-dicarboxylic acid are reacted, in a manner analogous to that described in Example 1, with thionyl chloride to give the corresponding acid chloride and the latter is then reacted with 10.9 g of 2-aminophenol. The resulting reaction mixture is concentrated to dryness in vacuo and the residue is recrystallized from nonane with the aid of active charcoal. 16 g, corresponding to 80% of theory, of the compound of the formula

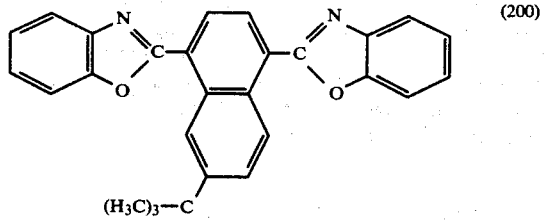

(200)

are obtained in the form of pale yellow needles with a melting point of 194°–195° C. After recrystallizing once from nonane, the melting point remains unchanged.

Analysis: $C_{28}H_{22}N_2O_2$. Calculated: C, 80.36; H, 5.30; N, 6.69. Found: C, 80.35; H, 5.48; N, 6.80.

The compounds of the formula

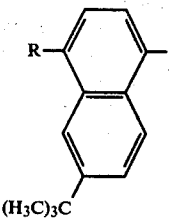

(201)

which are listed in Table II are prepared in an analogous manner from 6-tert.-butyl-naphthalene-1,4-dicarboxylic acid and the correspondingly substituted 2-aminophenols.

TABLE II

| Compound No. | Structure of R | Melting point, °C. |
|---|---|---|
| (202) | H₃C-[benzoxazole] | 207–208 |
| (203) | H₃COOC-[benzoxazole] | 275≅276 |
| (204) | H₅C₂OOC-[benzoxazole] | 254–255 |
| (205) | H₃COOC-[benzoxazole] | 202–203 |
| (206) | Cl-[benzoxazole] | 255–256 |
| (207) | H₅C₂ O₂S-[benzoxazole] | 189–191 |
| (208) | H₃C—O₂S-[benzoxazole] | 270–272 |
| (209) | H₃C-[benzoxazole]-CH₃ | 203–205 |
| (210) | (H₃C)₃C-[benzoxazole] | 178–180 |

EXAMPLE 3

63.6 g of the sodium salt of 1,4-dicarboxynaphthalene-6-sulphonic acid, together with 44 g of 2-aminophenol and 12 g of boric acid, are suspended in 250 ml of ®Aroclor 1221 (chlorinated biphenyl of Messrs. Monsanto, containing 21% of chlorine). The reaction mixture is heated to the boil (about 280° C.) whilst stirring and passing in nitrogen and the water formed is distilled off continuously. After boiling for three hours, the yellow-green suspension is allowed to cool to room temperature, whilst stirring, and is diluted with about 250 ml of chlorobenzene. The reaction mixture is now filtered and the material on the filter is washed with about 200 ml of chlorobenzene and dried in vacuo at 130° C. 91 g, corresponding to 98% of theory, of the compound of the formula

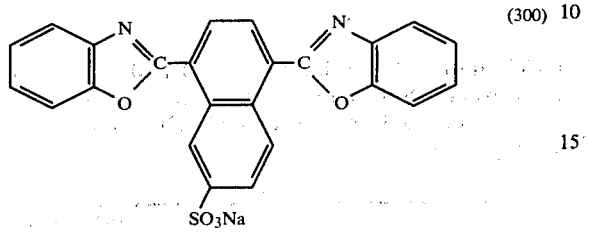

(300)

are obtained in the form of a yellow-green powder which melts at above 320° C. After recrystallising once from a mixture of water/alcohol (1:1) with the aid of active charcoal, pale yellow crystals which melt at above 320° C. are obtained.

Analysis: $C_{24}H_{13}O_5N_2S$, Na. Calculated: C, 62.07; H, 2.82; N, 6.03; S, 6.90. Found: C, 62.36; H, 3.01; N, 5.94; S, 6.87.

The sodium salt of 1,4-dicarboxynaphthalene-6-sulphonic acid, of the formula

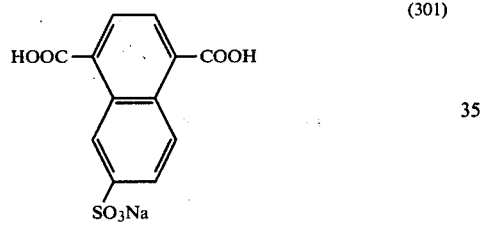

(301)

which is used as the starting material can be prepared as follows:

216 g of naphthalene-1,4-dicarboxylic acid are dissolved in 1,000 ml of sulphuric acid monohydrate, whilst stirring, and the reaction mixture is kept at 110° C. for 1½ hours. The reaction mixture is then cooled to 10° C. and poured onto ice and sodium chloride is added. The product which has precipitated out is filtered off, washed with sodium chloride solution until neutral and recrystallized from water with the aid of active charcoal. 259 g, corresponding to 81% of theory, of the compound of the formula (301) are obtained in the form of colourless needles with a melting point of 361° to 365° C. After recrystallising once from water, the product melts at 379° to 381° C.

Analysis: $C_{12}H_7O_7SNa$. Calculated: C, 45.29; H, 2.22; S, 10.07; Na, 7.22. Found: C, 44.98; H, 2.34; S, 9.73; Na 6.99.

EXAMPLE 4

20 g of the sodium sulphonate of the formula (300) are suspended in 500 ml of chlorobenzene and 0.5 ml of dimethylformamide and 100 ml of thionyl chloride are added, whilst stirring. The reaction mixture is kept under reflux (110°–115° C.) for three hours, during which time hydrogen chloride escapes. The excess thionyl chloride is then distilled off and the reaction mixture is freed, by filtration, from the sodium chloride which has formed. The reaction solution is now concentrated to dryness in vacuo. 17.8 g, corresponding to 91% of theory, of the compound of the formula

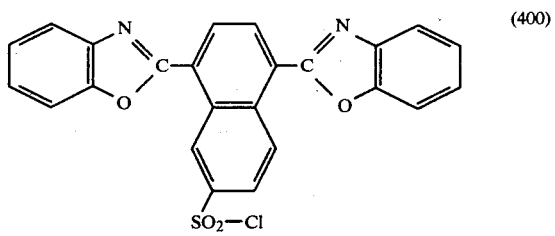

(400)

are obtained in the form of a yellow-green powder with a melting point of 238°–242° C.

17.8 g of the crude sulphonic acid chloride of the formula (400), thus obtained, are dissolved in 500 ml of dimethylformamide and the solution is kept under reflux for three hours. 300 ml of dimethylformamide are then distilled off and the reaction mixture is cooled to room temperature. The reaction solution is now slowly diluted with 200 ml of alcohol, the reaction product precipitating as crystals. 16.5 g, corresponding to 87% of theory, of the compound of the formula

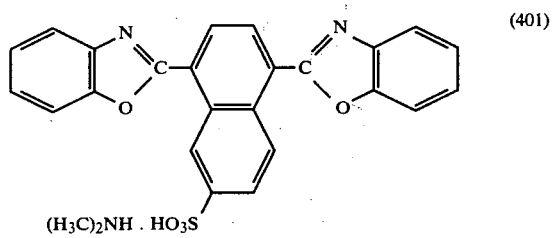

(401)

are obtained in the form of yellow-green crystals which melt at above 300° C. After recrystallising once from dimethylformamide, small pale yellow needles which melt at above 300° C. are obtained.

Analysis: $C_{26}H_{21}N_3O_5S$. Calculated: C, 64.05; H, 4.34; N, 8.62; S, 6.58. Found: C, 64.14; H, 4.38; N, 8.69; S, 6.67.

EXAMPLE 5

18 g of the crude sulphonic acid chloride of the formula (400) are taken up in 500 ml of chlorobenzene and the mixture is heated under reflux. 10 g of n-butylaniline, dissolved in 200 ml of chlorobenzene, are added dropwise in the course of 30 minutes. The reaction mixture is then kept under reflux overnight, decolorised with active charcoal and concentrated to about 200 ml. The reaction product crystallises out as small yellow needles. 15 g, corresponding to 76.1% of theory, of the compound of the formula

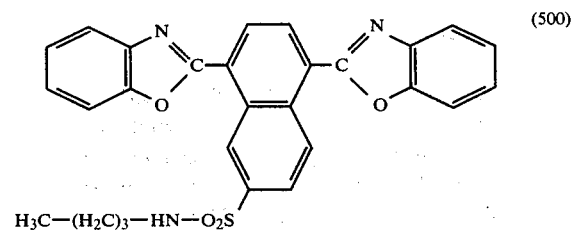

(500)

are obtained in the form of small yellow needles with a melting point of 221°–225° C. After recrystallising once from chlorobenzene, the product melts at 225° to 226° C.

Analysis: $C_{28}H_{23}O_4N_3S$. Calculated: C, 67.59; H, 4.66; N, 8.45; S, 6.44. Found: C, 67.38; H, 4.79; N, 8.17; S, 6.59.

The compounds of the formula

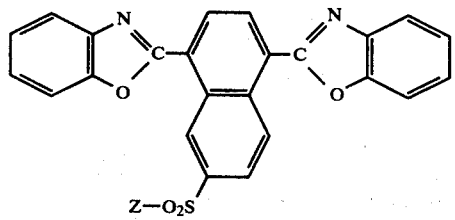

(501)

which are listed in Table III are prepared in an analogous manner from the sulphonic acid chloride of the formula (400) and corresponding amines.

TABLE III

| Compound No. | Structure of Z | Melting point, °C. |
|---|---|---|
| (502) | $-NH_2$ | 306–308 |
| (503) | $-NH-CH_2-CH_3$ | 271–272 |
| (504) | $-N(CH_2-CH_2-OH)_2$ | 214–215 |
| (505) | $-N\underset{\diagdown\diagup}{\diagup\diagdown}N-CH_2-CH_2-OH$ | 226–227 |

EXAMPLE 6

8.2 g of the sulphonamide of the formula (505) are taken up in 150 ml of chlorobenzene and the mixture is heated under reflux. A clear solution forms. 4.2 g of dimethyl sulphate, dissolved in 50 ml of chlorobenzene, are added dropwise in the course of 10 minutes. The reaction mixture is kept under reflux for 30 minutes, during which time the reaction product precipitates out as crystals. The reaction product is filtered off hot, washed with hot chlorobenzene and dried in vacuo at 100° C. 9.9 g, corresponding to 98% of theory, of the compound of the formula

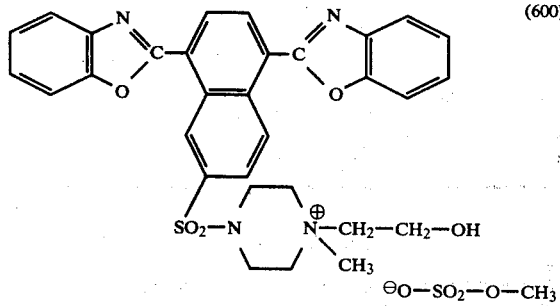

(600)

are obtained in the form of small pale yellow needles with a melting point of 236° to 270° C. (decomposition).

Analysis: $C_{32}H_{32}O_9N_4S_2$. Calculated: C, 56.46; H, 4.74; N, 8.23. Found: C, 56.39; H, 4.49; N, 8.29.

EXAMPLE 7

14.5 g of 1,4-dicarboxynaphthalene-6-methylsulphone in 200 ml of toluene are heated with 20 ml of thionyl chloride and 0.5 ml of dimethylformamide for two hours under reflux. Whilst passing nitrogen into the mixture, 75 ml of toluene, together with the excess thionyl chloride, are distilled off and replaced by fresh toluene. A solution of 10.9 g of 2-aminophenol and 18.2 g of N,N-dimethylaniline in 100 ml of toluene is added in the course of 15 minutes, at 70° to 80° C., to the acid chloride solution which has been obtained and the reaction mixture is stirred at this temperature for two hours. Half of the toluene is then distilled off, whilst passing in nitrogen, and 300 ml of 1,2,3-trichlorobenzene and 2 g of zinc chloride are added to the residue. The toluene which is still present is distilled off, whilst passing in nitrogen, and the reaction mixture is heated to 210° C. for two hours, during which time 200 ml of trichlorobenzene and water distil off. The residual mixture is cooled to room temperature and diluted with isopropyl alcohol. The reaction product which has crystallised out is filtered off, washed with isopropyl alcohol and dried in vacuo at 100° C. 14 g, corresponding to 63.6% of theory, of the compound of the formula

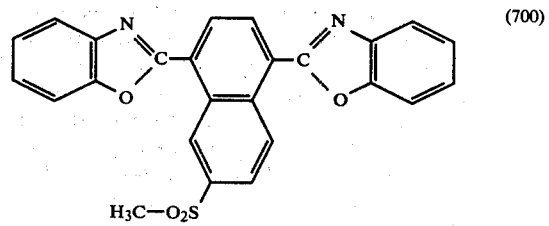

(700)

are obtained in the form of a yellow crystalline powder with a melting point of 290° to 294° C. After recrystallising once from dichlorobenzene with the aid of active charcoal, the product melts at 294° to 295° C.

Analysis: $C_{25}H_{16}O_4N_2S$. Calculated: C, 68.17; H, 3.66; N, 6.36; S, 7.28. Found: C, 67.91; H, 3.70; N, 6.22; S, 7.42.

1,4-Dicarboxynaphthalene-6-methylsulphone of the formula

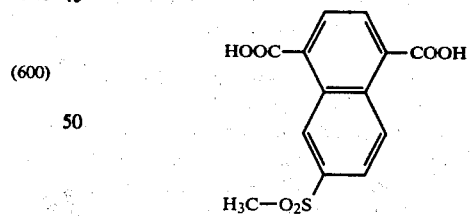

(701)

which is used as the starting material can be prepared as follows:

96 g of the sodium salt of 1,4-dicarboxynaphthalene-6-sulphonic acid of the formula (301) are suspended in 600 ml of chlorobenzene and 5 ml of dimethylformamide are added. The reaction mixture is heated to 90° C. and, at this temperature, 150 ml of thionyl chloride are added dropwise in the course of 30 minutes. The mixture is then kept under reflux (110°–115° C.) for four hours, during which time hydrogen chloride escapes. The excess thionyl chloride is then distilled off and the sodium chloride which has formed is removed by filtration. The reaction solution is now concentrated to dryness in vacuo. About 105 g, corresponding to 100% of theory, of the compound of the formula

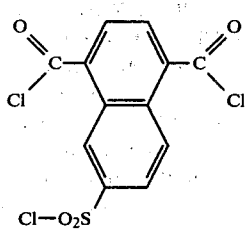
(702)

are obtained in the form of a colourless crystalline powder with a melting point of 123° to 126° C. After recrystallising once from cyclohexane, the product melts at 127° to 128° C.

Analysis: $C_{12}H_5Cl_3O_4S$ Calculated: C, 40.99; H, 1.43; Cl, 30.25; S, 9.12. Found: C, 41.00; H, 1.32; Cl, 30.11; S, 9.01.

209 g of the compound, obtained above, for the formula (702), dissolved in 1,000 ml of absolute dioxane, are added dropwise to a solution, which has been heated to 80° C., of 529 g of sodium sulphite heptahydrate in 1,000 ml of water. The pH value is kept at between 8 and 9 by adding a 30% strength aqueous solution of sodium hydroxide dropwise at the same time. The reaction mixture is then further stirred overnight at 80° C. and pH 9 and is then freed from dioxane by distillation, cooled and acidified with 600 ml of concentrated hydrochloric acid. The sodium salt of the sulphinic acid of the formula

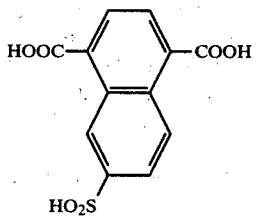
(703)

which has precipitated, is filtered off and washed with a saturated aqueous solution of sodium chloride until neutral.

The resulting crude product is then dissolved in 2,000 ml of 2 N sodium hydroxide solution at 80° C., the pH being adjusted to 7. 500 g of dimethyl sulphate are now added dropwise at this temperature and the pH value is kept at between 6 and 8 by adding a 30% strength aqueous solution of sodium hydroxide at the same time. The pH value is then adjusted to 7 and the reaction mixture is diluted with 1,000 ml of dioxane and further stirred overnight at 80° C. 500 ml of 30% strength sodium hydroxide solution are now added dropwise and, at the same time, the reaction solution is freed from dioxane by distillation. After two hours under reflux, the reaction solution is cooled to room temperature and acidified with 1,000 ml of concentrated hydrochloric acid. The reaction product which has precipitated is filtered off, washed with water until neutral and dried in vacuo at 100° C. 159 g, corresponding to 90% of theory, of 1,4-dicarboxynaphthalene-6-methylsulphone of the formula (701) are obtained in the form of a yellow crystalline powder with a melting point of 265° to 270° C.

After recrystallising once from water, the product melts at 270° to 272° C.

Analysis: $C_{13}H_{10}O_6S$. Calculated: C, 53.06; H, 3.43; S, 10.89. Found: C, 53.01; H, 3.41; S, 10.66.

The compounds of the formula

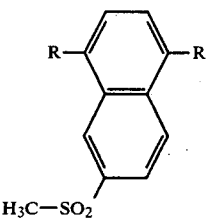
(704)

which are listed in Table IV are prepared in an analogous manner from 1,4-dicarboxynaphthalene-6-methylsulphone and correspondingly substituted 2-aminophenols.

TABLE IV

| Compound No. | Structure of R | Melting point, °C. |
|---|---|---|
| (705) | H3C- (benzoxazole) | 268–269 |
| (706) | H3COOC- (benzoxazole) | 289–291 |
| (707) | H5C2OOC- (benzoxazole) | 281–282 |
| (708) | H3COOC- (benzoxazole) | 282–285 |
| (709) | Cl- (benzoxazole) | 270–272 |
| (710) | H3C- (dimethyl benzoxazole) | 254–255 |
| (711) | (H3C)3C- (benzoxazole) | 183–185 |

EXAMPLE 8

100 parts of polyester granules consisting of polyterephthalic acid ethylene glycol ester are intimately mixed with 0.05 part of the compound of the formula (102) and the mixture is melted at 285° C., whilst stirring. After the spinning composition has been spun through conventional spinnerets, strongly brightened polyester fibres are obtained. If a compound of the formula (100), (103), (105), (107), (706) or (707) is used in place of the compound of the formula (102), similar results are obtained.

EXAMPLE 9

A polyester fabric (for example "Dacron") is padded at room temperature with an aqueous dispersion which contains, per liter, 2 g of the compound of the formula (100) and 1 g of an addition product of about 8 mols of ethylene oxide with 1 mol of p-tert.-octylphenol and dried at about 100° C. The dry material is then subjected to a heat treatment at 220° C. for a short time. The material treated in this way has a considerably whiter appearance than the untreated material.

If a compound of the formula (103) is employed in place of the compound of the formula (100), similar results are obtained.

EXAMPLE 10

Using a liquor ratio of 1:20, a fabric of polyamide fibres (for example "Perlon-Helanca") is washed for 15 minutes in a liquor which is at 55° C. and contains, per liter, 0.04 to 0.016 g of a brightener of the formula (401) and 4 g of a washing agent of the following composition: 15.7% of an alkyl arylsulphonate, 3.7% of a fatty alcohol sulphonate, 2.7% of coconut acid monoethanolamide, 39.0% of sodium tripolyphosphate, 4.0% of sodium silicate, 2.0% of magnesium silicate, 1.0% of carboxymethylcellulose, 0.5% of the sodium salt of ethylene-diaminetetraacetic acid (EDTA) and 6.7% of water, made up to 100% with sodium sulphate.

The fabric is then washed for ½ minute under running water and dried in a drying cabinet at 60° C. for 20 minutes.

The fabric displays a strong brightening effect with good fastness to light.

The washing agent of the above composition can also contain the brightener of the formula (401) directly incorporated therein.

Similarly good effects are also achieved when the compound of the formula (300) is used.

What is claimed is:

1. A 1,4-bis-[oxazol-2'-yl]-naphthalene, of the formula

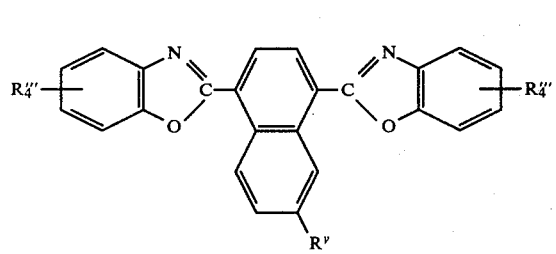

in which $R^v$ denotes chlorine, and $R_4'''$ denotes hydrogen, halogen in the 5-position or 6-position, alkyl with 1 to 4 carbon atoms or —COOY, wherein Y represents hydrogen, a salt-forming cation or alkyl with 1 to 4 carbon atoms, or denotes alkylsulphonyl with 1 to 4 carbon atoms.

2. A 1,4-bis-[oxazol-2'-yl]-naphthalene according to claim 1, of the formula

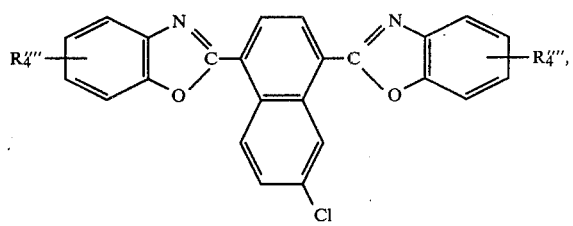

in which $R_4''''$ denotes hydrogen or, in the 5-position or 6-position, alkyl with 1 to 4 carbon atoms or —COOY, wherein Y represents alkyl with 1 to 4 carbon atoms.

3. The 1,4-bis-[oxazol-2'-yl]-naphthalene according to claim 1, of the formula

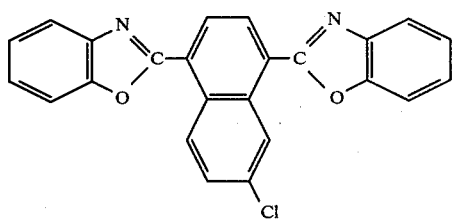

4. The 1,4-bis-[oxazol-2'-yl]-naphthalene according to claim 1, of the formula

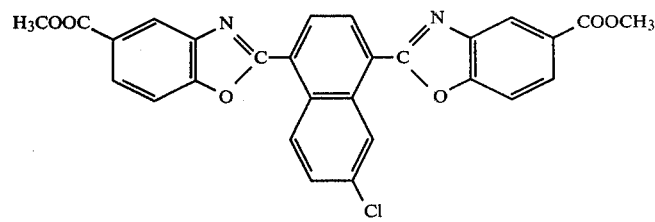

5. The 1,4-bis-[oxazol-2'-yl]-naphthalene according to claim 1, of the formula

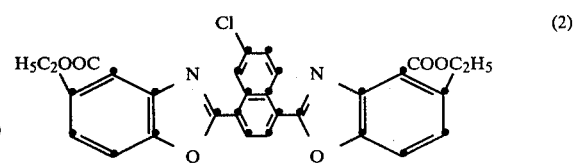

(2)

6. Process for optically brightening organic materials, wherein a compound as defined in one of claim 1 is incorporated into these materials or is applied to the surface thereof.

7. Process according to claim 6, wherein a compound as defined in claim 2 is incorporated into the materials or applied to the surface thereof.

8. Process according to claim 6 for optically brightening materials made of polyester.

9. Process according to claim 8, wherein compounds as defined in claims 3 or 4 are incorporated into the polyester or applied to the surface thereof.

10. Process according to claim 6, wherein 0.001 to 2%, of the brightener, based on the weight of the material to be optically brightened, is applied to the materials to be brightened or is incorporated into these materials.

* * * * *